United States Patent [19]
Easterling

[11] Patent Number: 6,031,005
[45] Date of Patent: Feb. 29, 2000

[54] COMPOSITION AND METHOD FOR TREATING PEYRONIE'S DISEASE AND RELATED CONNECTIVE TISSUE DISORDERS

[76] Inventor: W. Jerry Easterling, 8400 Blanco Rd., No. 204, San Antonio, Tex. 78216

[21] Appl. No.: 09/128,103

[22] Filed: Aug. 3, 1998

[51] Int. Cl.[7] .................................................. A61K 31/135
[52] U.S. Cl. ............................................................. 514/654
[58] Field of Search ............................................. 514/654

[56] References Cited

U.S. PATENT DOCUMENTS

| | | |
|---|---|---|
| 4,338,300 | 7/1982 | Gelbard . |
| 5,139,944 | 8/1992 | Sawyer . |
| 5,242,391 | 9/1993 | Place . |
| 5,474,535 | 12/1995 | Place . |
| 5,731,339 | 3/1998 | Lowrey . |
| 5,773,020 | 6/1998 | Place . |

FOREIGN PATENT DOCUMENTS

| | | |
|---|---|---|
| 9006583 | 9/1991 | South Africa . |

OTHER PUBLICATIONS

Levine, et al Intralesional Verapamil Injection for the Treatment of Peyronie's Disease:, Journal of Urology; vol. 151, 1522–1524; Jun. 1994.

Levine, "Treatment of Peyronie's Disease with Intralesional Verapamil Injection"; vol., 58, 395–399; Oct., 1997.

Rehman et al; "Use of Intralesional Verapamil to Dissolve Peyronie's Disease Plaque: A Long–Term Single–Blind Study"; Urology, vol. 51, 620–626.

H. Willmann, et al; "Lecithin Organogel as Matrix for Transdermal Transport of Drugs"; Journal of Pharmaceutical Science, vol. 81, No. 9, Sep. 1992.

Alici, B. et al., Cerrahpas Tip Dergisi, 28(1), pp. 33–36 (abstract), Jan. 3, 1997.

*Primary Examiner*—Phyllis G. Spivack
*Attorney, Agent, or Firm*—David G. Henry

[57] ABSTRACT

The invention is of a topical medicament and associated methodology for use thereof, such that Peyronie's disease may be effectively, cost effectively, and painlessly treated. The primary active ingredient is a calcium channel blocker, the preferred such ingredient being verapamil.

2 Claims, No Drawings

COMPOSITION AND METHOD FOR TREATING PEYRONIE'S DISEASE AND RELATED CONNECTIVE TISSUE DISORDERS

BACKGROUND OF THE INVENTION

1. Field of the Invention

Applicant's invention relates to medicaments and treatment procedures relating to Peyronie's disease and related connective tissue maladies.

2. Background Information

A. Peyronie's Disease

The initial focus of the present invention—Peyronie's disease—has likely plagued men for time immemorial, but has been recognized as a distinct malady for no less than 400 years. Peyronie's disease was first described in 1743 by a French surgeon, Francois de la Peyronie. The disease was written about as early as 1687 and was oftentimes associated with impotence.

Peyronie's disease manifests itself in various manners, and to varying degrees of severity. The most common manifestation of Peyronie's disease is in the form of a "lump," "plaque" or "hard" area in the non-erect penis. With or without these palpable symptoms, painful erections and penile disfigurement are often associated with the malady.

The pain and disfigurement associated with Peyronie's disease relate to the physical structure of the penis in which is found two erectile rods, called the corpora cavernosa, a conduit (the urethra) through which urine flows from the bladder, and the tunica which separates the cavernosa from the outer layers of skin of the penis. A person exhibiting Peyronie's disease will have formation(s) of plaque or scar tissue between the tunica and these outer layers of the skin. The scarring or plaque accumulation of the tunica reduces its elasticity causes such that, in the affected area, it will not stretch to the same degree (if at all) as the surrounding, unaffected tissues. Thus, the erect penis bends in the direction of the scar or plaque accumulation, often with associated pain of some degree.

Peyronie's disease often occurs in a mild form and heals spontaneously in 6 to 15 months. However, in severe cases, the hardened plaque substantially reduces penile flexibility and causes excruciating pain as the penis is forced into a highly arcuate or even serpentine configuration. A plaque on the top of the shaft (most common) causes the penis to bed upward; a plaque on the underside causes it to bend downward. In some cases, the plague develops on both top and bottom, leading to indentation and shortening of the penis.

In all but minor manifestations of Peyronie's disease, the victim has some degree of sexual dysfunction. In more severe cases, sexual intercourse is either impossible, or is so painful as to be effectively prohibitive.

While plaque of Peyronie's disease is itself benign, or noncancerous, this is of little solace to sufferers of the disease.

Empirical evidence indicates an incidence of Peyronie's disease in approximately one percent of the male population. Although the disease occurs mostly in middle-aged men, younger and older men can acquire it. About 30 percent of men with Peyronie's disease also develop fibrosis (hardened cells) in other elastic tissues of the body, such as on the hand or foot. Common example of such other conditions include Dupuytren's contracture of the hand and Ledderhose Fibrosis of the foot.

Many researchers believe the plaque of Peyronie's disease develops following trauma to the penis (hitting or bending) that causes localized bleeding inside the penis. If the penis is abnormally bumped or bent, an area where the septum attaches to the elastic fibers surrounding the corpora cavernosa may stretch beyond its normal limit, injuring the lining of the erectile chamber and, for example, rupturing small blood vessels. Also, as a result of aging, diminished elasticity near the point of attachment to the septum may tend to increase the chances of injury of this nature.

Such a damaged area may heal slowly or abnormally because of repeated trauma to the same area and/or because of the natural, minimal amount of blood-flow in the sheath-like fibers of the elastic structures of the penis. In cases of Peyronie's disease which tend to heal within about a year, the plaque does not tend to advance beyond an initial inflammatory phase. In cases that persist for longer periods, the plaque typically undergoes fibrosis, or the formation of tough fibrous tissue, and even calcification, or the formation of calcium deposits.

While trauma might explain acute cases of Peyronie's disease, it does not explain why most cases develop slowly and with no apparent traumatic event. It also does not explain why some cases disappear quickly, and why similar conditions, such as Dupuytren's contracture, do not seem to result from severe trauma.

In some cases, men who are related by blood tend to develop Peyronie's disease, which suggests a possible genetic predisposition to Peyronie's disease.

D. Present Treatment

Because the cause(s) and development of Peyronie's disease are not well understood, physicians to this day treat the disease with a largely experimental approach—they discontinue anything which lacks apparent efficacy, and continue anything that seems to help.

Surgery is the only approach to treating Peyronie's disease which appears to have predictably repeatable efficacy. Surgery is usually only indicated in long-term cases where the disease is stabilized and the deformity prevents intercourse and/or causes extreme pain. However, complications can develop from surgery, including a permanent shortening of the penis.

Attempts at simple plaque excision were described in the 19th century by MaClellan, Regnoli and Huitfield, but by the early 20th century most authors described this technique as disastrous. For this reason Young developed a procedure that simply "freed" the plaque from the tunica albuginea in order to improve erectile dynamics. Lowsely and Boyce then re-explored the technique of simple plaque excision by adding the interposition of a "pat-pad" graft into the defect. Although many others continued to report success with this technique, it failed to gain general acceptance as the treatment of choice.

In 1995 Nesbit described the correction of congenital penile curvature with multiple elliptical excisions of the corporeal tunica. To this day, many surgeons prefer this technique for the correction of the Peyronie's bend. However, the inevitable penile shortening led Devine and Horton (1974) to experiment with further grafting procedures. Having experimented with fascial, arterial and venous patches in dogs, they came to the conclusion that dermal grafts were the least likely to "contract" and so reproduce the defect. To this day, many other grafting materials have been tried including autologous vein, temporoparietal fascia, tunica vaginalis, gortex and dacron.

The cost of the various surgical approaches to Peyronie's disease (no less than around $6,500) is, alone, often a deterrent to many Peyronie's disease sufferers in adopting this particular approach to treatment. While surgical intervention was, prior to the present invention, the most likely effective treatment in any given case of Peyronie's disease, the condition does often reappear, even after surgery.

The other, presently known, non-surgical approaches to Peyronie's disease treatment are many and varied, although they are all largely ineffective. Attempts to dissolve the plaques by direct intra-lesional injections have been tried since the late 19th century. Walsham and Spencer injected both mercury and iodide and intra-lesional injections of fibrinolysins were used in the 1820's. Teasley introduced the concept of intra-leasional steroid injections in 1954, although the pain caused by the high injection pressures led many surgeons to perform the procedure under general anaesthetic. In 1959 Hinman developed a "high pressure" screw-threaded injection device that was somewhat effective in certain cases, and could be used with no anaesthesia, but still lacked predictable efficacy. More recently, intra-lesional injections of agents such as Verapamil and clostridial collagenase Have been tried, but with very limited success.

Of the injection methodologies, those involving clostridial collagenase appear to exhibit the most consistent efficacy, though still quite limited in effect and duration. Collagenase is likely effective through its ability to dissolve collagen, the major component of the plaque of Peyronie's disease.

Both external beam radiation treatment and intra-lesional implantation of radium seeds have been tried since the turn of the 20th century. In 1921, Sonntag reviewed this practice and claimed that these treatments were actively detrimental. Despite this, radiation therapy had been used in many clinics over the years and some authorities still claim that success can be anticipated if a radiation regimen is initiated early in the course of the disease. Radiation treatment is also said to be particularly effective for treating patients whose predominant symptom is pain (as opposed to severe disfigurement).

As technologies have evolved, so have the associated energy sources which have been applied to treat Peyronie's disease. Early in the 20th century, diathermy current was used to generate heat to treat the plaque and eventually low voltage electrical devices were developed and sold for use in the home. Perhaps the most imaginative variant was the technique known as histamine iontophoresis. This combined the use of electrodes with a "plaque busting" solution that was supposedly absorbed into the penis when an electrical gradient was applied. In more recent times, both ultraviolet light and local ultrasound have surfaced and submerged in the treatment history.

Not surprisingly, the inevitable application of laser technology has recently emerged as a means of "vaporizing" the plaque. Again, the efficacy of this latest treatment is open to serious question.

The staggering array of treatment options for Peyronie's disease (failed attempts, really), and the invested effort, cost and intellectual energy which they represent, are testament to the serious need that remains for an effective treatment for Peyronie's disease, and one which patients can tolerate from cost, comfort and convenience perspectives.

All-in-all, there is simply no truly effective treatment of Peyronie's disease—a disease which often produces such severe discomfort and distress that sufferers have been willing to endure such treatments as penile injections.

SUMMARY OF THE INVENTION

It is an object of the present invention to provide a novel a medicament useful in the treatment of connective tissue disorders, exemplified by Peyronie's disease.

It is another object of the present invention to provide a novel medicament and unobvious medicament useful in the treatment of connective tissue disorders, exemplified by Peyronie's disease, which medicament obviates the need for such dramatic treatments intra-penile injections and surgery.

It is another object of the present invention to provide a novel and unobvious medicament useful in the treatment of connective tissue disorders, exemplified by Peyronie's disease, which medicament is more effective that existing means for treatment.

In satisfaction of these and related objectives, Applicant's present invention provides a topical medicament and associated methodology for use thereof, through the use of which Peyronie's disease and related connective tissue disorders may be effectively, cost effectively, and painlessly treated.

DETAILED DESCRIPTION OF THE PREFERRED EMBODIMENT

The medicament of the present invention is a topical gel which has repeatably effected a complete reversal of Peyronie's disease symptoms in a number of experimental applications.

In the preferred embodiment, the (apparently) primary active ingredient of the topical gel is Verapamil Hydrochloride, USP (a diphenylalkylamine). However, it should be understood that other calcium channel blockers (topically applied in a similar composition) may provide similar relief. Other such calcium channel blockers include benzothiazepines (Diltiazem, for example), dihydropyridines (Amlodipine, Felodipine, Isradipine, Nicardipine, Nifedipine, Nimodipine, or Nisoldipine), and the fast sodium inward channel inhibitor—Bepridil.

The preferred Verapamil-based gel of the present invention includes two constituent preparations—Lecithin Isopropyl Pulmitate Solution and Pluronic F1 27 Gel 20%—the preferred mode of preparation of which is as follows:

I. Lecithin Isopropyl Pulmitate Solution (To Make 220 ml).

Lecithin Soya Granular 100 g

Isopropyl Palmitate, NF, Cosmetic Grade 117 ml

Sorbic Acid, NF-FCC Powder 0.66 g

A. Mix Lecithin Soya Granular and Sorbic Acid in a plastic or glass container.

B. Add Isopropyl Palmitate (or Isopropyl Myristate, Cosmetic Grade, as an acceptable substitute) and allow to stand at room temperature until a liquid of syrupy consistency forms. All lecithin soya and sorbic acid will appear to have dissolved in the palmitate.

C. Label and mark the expiration date to be six (6) months.

II. Pluronic F127 Gel 20%—(To Make 100 ml)

Pluronic F127, NP 20 g

Potassium Sorbate, NF 0.3 g

Purified Water, q.s. 100 ml

A. Mix the Pluronic F127 with the Potassium Sorbate.

B. Place in a glass beaker and add refrigerated Purified Water to produce a final volume of precisely 100 ml.

C. Allow to stand under refrigeration (39–42° C. until solution is clear and all materials are dissolved.

D. Volume will have decreased due to water absorption by the Plutonic F127 after Step C, so one should correct volume to 100 ml by adding refrigerated purified water.

E. Place in refrigerated storage, and label with an expiration date of six (6) months.

Once the Lecithin Isopropyl Pulmitate Solution and Pluronic F1 27 Gel 20% are prepared (or otherwise obtained), the Verapamil gel of the present invention is prepared as follows:

Verapamil Topical Gel (40 mg/0.50 ml) (To Make 45 ml)
Verapamil Hydrochloride, USP 3.6 g
Lecithin Isopropyl Palmitate Stock Solution 15 ml
Ethoxy Diglycol 5 ml
Pluronic F127 Gel 20% Stock Solution q.s. to 45 ml (approximately 23 ml)

A. Weigh Verapamil and add to a glass beaker.
B. Add Ethoxy Diglycol and stir to mix well.
C. Place Verapamil/Ethoxy Diglycol suspension on a hot-plate and heat at 50–55° C. with stirring until verapamil dissolves and a clear solution exists. Remove from hot plate.
D. Add Lecithin Isopropyl Palmitate Stock Solution and still until well mixed.
E. Draw verapamil/isopropyl palmitate (step 4) into a 60 cc luer-lock syringe using a 16G-1 needle.
F. Draw Pluronic F127 Gel 20% Stock Solution into a separate 60 cc luer-lock syringe using a 16G-1 inch needle.
G. Dispel all air from both 60 cc syringes.
H. Connect the two 60 cc syringes using a luer-lock-to-luer-lock adapter.
I. Mix the contents of the two 60 cc syringes by forcing the plungers in order to pass the contents of one syringe into the other syringe. Repeat this process at least twenty five (25) times, leaving the total contents in one of the 60 cc syringes.
J. Prepare 45 1.0 ml oral/topical amber syringes by removing the plunger from each syringe.
K. Affix a luer-lock/oral adapter to the 60 cc syringe containing the 45 ml of medication. Place the tip end of each oral/topical amber syringe into the open end of the luer-lock/oral adapter and fill each syringe to the 1.0 ml mark. Place a cap on each filled syringe and set aside.
L. Using an 18G needle, pierce each 1 ml syringe, containing the 1.0 ml of medication, just below the medication level to allow the plungers to be reinserted into the syringes.
M. Reinsert the plunger into each 1 ml filled syringe.
N. Package in a light-resistant container and label "Do Not Refrigerate. Store At Room Temperature."
O. Dispense to patients with application instructions.

The Verapamil topical gel of the present invention is dispensed, via the preferred mode of the present invention, in a 1.0 ml amber syringe which is graduated in 0.01 ml increments, with major graduations at 0.1 through 1.0 ml. The syringe is filled to the 1.0 ml mark with the gel (assuming a 1.0 ml syringe is used).

The recommended single dose of the present Verapamil gel contains (40 mg) of Verapamil and is contained in 0.50 ml of the preferred embodiment of the gel.

Syringes in which the present Verapamil gel is delivered to patients can be prepared with any number of doses, limited only by the capacity of the syringes.

Each syringe is capped with a removable tip that can be removed and replaced by simply pushing and pulling at the dispensing end of the syringe.

Packaging in which the filled syringes are dispensed to patients (and/or the syringes themselves) should be labeled with the following legend:

This medication must not be refrigerated.
Refrigeration may destroy the absorption qualities of the carrier agents(s).

The patient is to apply 0.50 ml of the present medicament twice each day, preferably in the morning and after a shower (or other cleansing) in the evening. Before each application, any remnant of the prior dose(s) must be completely removed and the area of prior application cleaned and dried before a new dose is applied.

For the first does of each syringe, the patient removes the syringe cap and dispels 0.50 ml by pushing the plunger to the 0.5 ml syringe mark. The second dose requires pushing the plunger to expel the remaining 0.5 ml of gel. One 1.0 ml syringe will, therefore, provide one day's dosage of the president medicament according to the preferred mode of practice of the present invention.

Once the medication is dispensed from the syringe, the patient should apply the medication by starting at the point where the plaque is heaviest, or where the curvature begins, and work out until the entire penile shaft has been covered with medication. Absorption is rapid which allows the patient to immediately dress.

Application to the entire penile shaft is important. In initial experimental use of the present medicament, localized application of the gel (solely to areas atop the suspected plaque) effected merely a change in the direction of the previous curvature. Subsequent application to the entire penile shaft in the same patients resulted in complete reversal of symptoms. This phenomena may be explained if plaque, to varying degrees, is present throughout the entire penile shaft, and not just localized to the point(s) of curvature.

During the treatment regimen, each patient's progress should be evaluated, at least every two weeks. If no results have occurred by the end of the 3rd week, the dose should be increased and/or the medicament applied more often than twice dialy.

Since Verapamil is an antihypertensive, the patient's blood pressure should be monitored after the first dose is applied at the physician's clinic. To date, however, no changes in blood pressure have been noted.

It should be noted that Verapamil, a calcium channel blocker, is commonly given orally or intravenously to treat cardiac arrhythmias and/or hypertension. Verapamil is even one of the substances which has been injected directly into the plaque of Peyronie's disease sufferers. However, despite the pain and psychological distress associated with penile injections of any kind, it has not heretofore occurred to anyone to compound a topical Verapamil preparation for use in treating Peyronie's disease. It appears that the very limited success of direct application of Verapamil to plaques through injection would have logically deterred practitioners from applying the same substance in a less direct manner—through topical application.

It is unclear how the medicament of the present invention works to relieve the symptoms of Peyronie's disease. The present inventor believes, however, that, upon successful absorption of the drug through the skin into the plaque, the calcium channel blocking properties of Verapamil causes the body to produce collagenase. Collagenase, in turn, dissolves the collagen of which the plaque is primarily formed.

However it works, the present medicament shows an astonishing efficacy, particularly considering the miserable failure of such closely related prior attempts at Peyronie's disease treatment. One patient involved in experimental evaluation of the present medicament exhibited a penile curvature in excess of 75 degrees—a condition which was both painful and which effectively rendered the individual completely sexually dysfunctional. After using the medicament of the present invention, in the prescribed manner, this patient's Peyronie Is disease symptoms were completely reversed in two week's time. Other experimental patients, albeit with less severe symptoms, have shown equally remarkable and complete recoveries.

While the initial dose of the preferred Verapamil gel has, to date, been 0.50 ml (containing 40 mg of Verapamil) applied twice daily, in the morning and at night, it is suspected that, once a patient receives relief, the plaque may re-form if the medication is stopped. In that event, continued use of the present medicament, perhaps at a lower dose, or less frequently, may be indicated.

Very recently, the medicament of the present invention has shown similarly remarkable results in the treatment of Dupuytren's contracture of the hand. The same medicament, applied in the same dosage form (except applied in the area of deformation of the hand) has completely reversed symptoms of the Dupuytren's contracture in approximately four week's time. This indicates that the present medicament has application well beyond the treatment of Peyronie's disease, and promises relief in any disease of similar mechanisms or physical manifestations as Peyronie's disease.

Although the invention has been described with reference to specific embodiments, particularly with respect to the particular active ingredient of the present medicament, this description is not meant to be construed in a limited sense, in particular to limit the scope of the appended claims to cover only those medicaments and associated modalities of treatment which include Verapamil as the calcium channel blocker, the function of which in the area of plaque appears to lie at the heart of the efficacy of the present medicament. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A medicament for use in the treatment of the connective tissue disorders of Peyronie's disease and Dupuytren's contracture comprising:

a carrier host agent for facilitating noninvasive transdermal application of said medicament to an affected bodily structure;

a diphenylalkylamine calcium channel blocker agent dissolved in said carrier host agent.

2. A method for treating the connective tissue disorders of Peyronie's disease and Dupuytren's contracture of the hand comprising the steps of:

selecting a composition comprising:
a carrier host agent for facilitating noninvasive transdermal application of said medicament to an affected bodily structure;
a diphenylalkylamine calcium channel blocker agent dissolved in said carrier host agent;

topically applying said composition to a bodily structure which exhibits symptoms of one or more of said connective tissue disorders.

* * * * *